United States Patent
Liu et al.

(10) Patent No.: US 9,279,095 B2
(45) Date of Patent: Mar. 8, 2016

(54) POLY(NITROGEN/AMINE) DERIVATIVES OF A NATURAL WAX AND OPHTHALMIC COMPOSITIONS

(71) Applicant: BAUSCH & LOMB INCORPORATED, Rochester, NY (US)

(72) Inventors: Xiaojun Michael Liu, Glen Allen, VA (US); Krista Fridman, Penfield, NY (US); Erning Xia, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 45 days.

(21) Appl. No.: 14/161,936

(22) Filed: Jan. 23, 2014

(65) Prior Publication Data

US 2014/0206764 A1 Jul. 24, 2014

Related U.S. Application Data

(60) Provisional application No. 61/756,206, filed on Jan. 24, 2013.

(51) Int. Cl.
| | |
|---|---|
| *A61K 31/14* | (2006.01) |
| *A61K 31/20* | (2006.01) |
| *C11C 3/04* | (2006.01) |
| *A61K 9/00* | (2006.01) |
| *A61K 47/18* | (2006.01) |
| *A61K 47/44* | (2006.01) |
| *A61L 12/14* | (2006.01) |
| *A61K 31/785* | (2006.01) |
| *A61K 35/644* | (2015.01) |
| *C08G 73/02* | (2006.01) |
| *A61K 36/00* | (2006.01) |

(52) U.S. Cl.
CPC .............. *C11C 3/04* (2013.01); *A61K 9/0048* (2013.01); *A61K 31/14* (2013.01); *A61K 31/785* (2013.01); *A61K 35/644* (2013.01); *A61K 47/186* (2013.01); *A61K 47/44* (2013.01); *A61L 12/142* (2013.01); *C08G 73/0206* (2013.01); *A61K 36/00* (2013.01)

(58) Field of Classification Search
CPC .................. A61K 31/14; A61K 31/785
See application file for complete search history.

(56) References Cited

U.S. PATENT DOCUMENTS

| | | | |
|---|---|---|---|
| 4,409,205 | A | 10/1983 | Shively |
| 5,209,927 | A | 5/1993 | Gressel et al. |
| 5,294,607 | A | 3/1994 | Glonek et al. |
| 5,300,287 | A | 4/1994 | Park |
| 6,172,017 | B1 | 1/2001 | Groemminger et al. |
| 6,486,215 | B2 | 11/2002 | Asgharian |
| 6,995,123 | B2 | 2/2006 | Ketelson et al. |
| 2005/0202097 | A1 | 9/2005 | Maskin |
| 2010/0086514 | A1 | 4/2010 | Liu et al. |

FOREIGN PATENT DOCUMENTS

WO 2010/077743 A1 7/2010

OTHER PUBLICATIONS

International Search Report and Written Opinion of the International Searching Authority mailed Apr. 17, 2014 in corresponding International Application No. PCT/US2014/012676 (10 pages).
Binman et al: Functionalization at the Double-Bond Region of Jojoba Oil. 8. Chemical Binding of Jojoba Liquid Wax to a Polymer Matrix via an Amine "Spacer"—JAOCS, vol. 73, No. 9 (1996) 13 pages.
Hoogenboom et al.: Scale-up of Microwave-Assisted Polymerizations in Batch Mode: The Cationic Ring-Opening Polymerization of 2-Ethyl-2-oxazoline—Macromol. Rapid Commun. 2006, vol. 27, pp. 1556-1560.
Tauhardt et al.: Linear Polyethyleneimine: Optimized Synthesis and Characterization—On the Way to "Pharmagrade" Batches—Macromol. Chem. Phys. 2011, vol. 212, pp. 1918-1924.
Nguyen et al.: Evaluation of polyether-polyethyleneimine graft copolymers as gene transfer agents Gene Therapy (2000), vol. 7, pp. 126-138.
Lambermont-Thijs et al.: Linear Poly(ethylene imine)s by Acidic Hydrolysis of Poly(2-oxazoline)s: Kinetic Screening, Thermal Properties, and Temperature-Induced Solubility Transitions Macromolecules 2010, vol. 43, pp. 927-933.

*Primary Examiner* — Zohreh Fay
(74) *Attorney, Agent, or Firm* — Toan P. Vo

(57) ABSTRACT

A poly(nitrogen/amine) derivative of a natural wax of formula I, and ophthalmic compositions and contact lens care solutions that contain the poly(nitrogen/amine) derivative of a natural wax of formula I. The invention is also directed to a method of treating a patient with dry eyes, the method comprising instructing a patient to administer one or more eye drops of the ophthalmic composition that includes a poly (nitrogen/amine) derivative of a natural wax of formula I.

20 Claims, No Drawings

POLY(NITROGEN/AMINE) DERIVATIVES OF A NATURAL WAX AND OPHTHALMIC COMPOSITIONS

FIELD OF THE INVENTION

The present invention relates to a poly(nitrogen/amine) derivative of a natural wax and ophthalmic compositions that include a poly(nitrogen/amine) derivative of a natural wax. The invention is also directed to the use of the ophthalmic compositions as a contact lens care solution, or as eye drops to treat ocular disorders.

BACKGROUND OF THE INVENTION

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort during use and at the end of the day. Accordingly, it is important to remove any debris from the lens surface for continued comfortable use with a lens care cleaning and disinfecting solution that contains one or more cleaning components. It can also be important that a lens care cleaning and disinfecting solution provide a contact lens consumer with some level of ocular comfort or hydration, particularly, consumers diagnosed with keratoconjunctivitis sicca, a condition often referred to as dry eye syndrome.

Dry eye is a common ophthalmological disorder affecting millions of people. A patient with dry eye may experience burning, a feeling of dryness, and persistent irritation. In severe cases, dry eye can seriously impair a person's vision. Also, as people age the lacrimal glands in the eye may produce less tears, resulting in eyes that become dry, inflamed, itchy, and gritty. More than 50% of total patients visiting ophthalmic clinics report dry eye syndromes. The elderly, particularly 70 to 80% of post-menopausal women suffer from ocular discomfort due to dry eye. Although it appears that dry eye may result from a variety of unrelated pathogenic causes, all presentations of the condition share a common feature, namely the breakdown of the precorneal tear film that results in dehydration of the exposed outer ocular surface and hence the symptoms described.

A number of approaches exist for the treatment of dry eye. One common approach has been to supplement the ocular tear film using artificial tears instilled throughout the day. Examples of the tear substitute approach include the use of buffered, isotonic saline solutions and aqueous solutions containing water-soluble polymers that render the solutions more viscous and thus less easily shed by the washing action of tear fluid. See, for example, U.S. Pat. No. 5,209,927 to Gressel et al.; U.S. Pat. No. 5,294,607 to Glonek et al.; and U.S. Pat. No. 4,409,205 to Shively.

Natural waxes are often found as trace components of triglyceride oils or can be extracted from certain botanical and animal sources. Sunflower and corn oils contain natural waxes, while jojoba, carnauba and candelillia are examples of waxes found naturally in a more pure form. Beeswax and lanolin are examples of natural waxes of insect and animal origin. These example waxes range from the liquid, unsaturated jojoba oil to the almost completely saturated sunflower wax. In order to control or modify various properties of natural oils and waxes such as water solubility, one can form alkoxylated derivatives. For example, by controlling the number of ethylene oxide (ETO) and/or propylene oxide (PO) units that one can attach to the hydroxyl function of the natural waxes various properties such as solubility and melting point can be modified. Generally, it has been found that the natural oils and waxes become more water soluble as the level of alkoxylation increases. Compounds that are ethoxylated, as well as propoxylated, become more water and alcohol soluble.

Lanolin also called Adeps Lanae, wool wax or wool grease, is a yellow waxy substance secreted by the sebaceous glands of sheep. Lanolin is also frequently, but incorrectly, referred to as wool wat even though it well known that lanolin is essentially devoid of glycerides and is in fact a wax, not a fat. Like many natural products, lanolin has a complex and variable composition. For example, a typical high purity grade of lanolin is composed predominantly of long chain waxy esters (ca. 97% by weight) the remainder being lanolin alcohols, lanolin acids and lanolin hydrocarbons. Lanolin's role in nature is to protect wool and skin against the ravages of climate and the environment—it also seems to play a role in integument hygiene. It is therefore not surprising that lanolin and its many derivatives are used extensively in products designed for the protection, treatment and beautification of human skin.

Poly(ethoxylate) lanolin or PEG lanolin is a commercially available. PEG lanolin is derived from lanolin by a chemical process that adds ethoxylate linkages to the hydroxyl functionality of lanolin. PEG lanolin is a flaky wax at room temperature with a slight yellow to amber color. PEG75 lanolin has polymer chains with a mean length of 75 ethylene oxide units, and the resulting compound has a weight average molecular weight (MW) of about 3500 dalton with a lanolin ester core and a polyethylene oxide chain. PEG75 lanolin is a water-soluble derivative of lanolin as a result of ethoxylation. The surrounding polyether chain allows water molecules to assemble around the non-polar and otherwise virtually water insoluble lanolin ester core. The resulting aqueous solutions are clear with a feint yellow color that increases with concentration, non-ionic and compatible with most physiological electrolytes, e.g. sodium chloride.

Jojoba is a shrub native to the Sonoran and Mojave deserts of Arizona, California, and Mexico. Jojoba is grown commercially for its oil, a liquid wax ester, expressed from the seed. The oil is rare in that it is an extremely long (C36-C46) straight-chain wax ester and not a triglyceride, making jojoba and its derivative jojoba esters more similar to human sebum and whale oil than to traditional vegetable oils. Jojoba oil is easily refined to be odorless, colorless and oxidatively stable, and is often used in cosmetics as a moisturizer and as a carrier oil for specialty fragrances. U.S. Patent Pub. No. 20050202097 describes a formulation for treatment of the symptoms of dry eye that includes natural jojoba wax, or components thereof, and is said to relieve ocular irritation and discomfort associated with dry eye.

Poly(ethoxylate) jojoba or PEG jojoba is available as a commercial source of an alkoxylated jojoba. Like PEG lanolin, PEG jojoba is derived from jojoba oil by a chemical process that adds ethoxylate linkages to the hydroxyl functionality of the oil. PEG jojoba is a flaky, off-white wax at room temperature. PEG150 jojoba has polymer chains with a mean length of 150 ethylene oxide units. PEG jojoba is a completely water-soluble derivative of jojoba oil as a result of ethoxylation.

U.S. patent application Ser. No. 12/571,465 filed Oct. 1, 2009 relates to contact lens care solutions with a cationic antimicrobial component, and a low molecular weight cationic or nitrogen/amine-based oligomer. The number average molecular weight of the cationic or nitrogen/amine-based oligomer is in the range of 500 daltons to 15,000 daltons, and is believed to compete with the cationic antimicrobial component for the pores or surface sites of contact lens materials. The result is a contact lens care solution with improved biocidal efficacy over time and improved comfort to the patient.

SUMMARY OF THE INVENTION

The invention is directed to a poly(nitrogen/amine) derivative of a natural wax of formula I

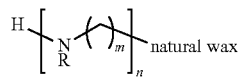
(I)

wherein R is —H, —CH$_3$, —C$_2$H$_5$, —OH and —CH$_2$OH; m is 2, 3, 4, 5 or 6; n is an integer from 8 to 110 if m is 2 or 3, and n is an integer from 6 to 60 if m is 4, 5 or 6. Some of the more preferred natural waxes include beeswax, lanolin, PEG lanolin, jojoba and PEG jojoba.

The invention is also directed to an ophthalmic composition comprising: 0.005 wt. % to 2.0 wt. % of a poly(nitrogen/amine) derivative of a natural wax of formula I. Some of the more preferred natural waxes include beeswax, lanolin, PEG lanolin, jojoba and PEG jojoba. Also, in some select embodiments, the ophthalmic composition will also include 0.002 w. % to 0.2 wt. % hyaluronic acid or 0.05 w. % to 0.5 wt. % hydroxypropyl guar. The invention is also directed to a method of treating a patient with dry eyes, the method comprising instructing a patient to administer one or more eye drops of an ophthalmic composition that includes a poly(nitrogen/amine) derivative of a natural wax of formula I.

The invention is also directed to a contact lens care solution comprising: 0.005 wt. % to 2.0 wt. % of a poly(nitrogen/amine) derivative of a natural wax of formula I. Again, some of the preferred natural waxes are selected from the group consisting of beeswax, lanolin, PEG lanolin, jojoba and PEG jojoba. In some select embodiments, the contact lens care solution will also include 0.002 w. % to 0.04 wt. % hyaluronic acid or 0.005 wt. % to 0.1 wt. % hydroxypropyl guar, and one or more antimicrobial components selected from the group consisting poly(hexamethylene biguanide), which is present from 0.5 ppm to 1.5 ppm; α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm; and alexidine, which is present from 1 ppm to 4 ppm.

DETAILED DESCRIPTION OF THE INVENTION

The term "contact lens care solution" is an aqueous-based, ophthalmically acceptable composition that can be used to clean and disinfect contact lenses, particularly contact lenses classified as silicon hydrogel lenses that are prescribed for weekly, bi-weekly or monthly use, rewet or comfort solutions for use with contact lenses, and lens packaging solutions. The term "ophthalmic composition" is an ophthalmically acceptable composition that includes contact lens care solutions as well as compositions particularly formulated to treat eye-related conditions such as dry eye, to relieve allergy-related symptoms and other eye comfort formulations and ophthalmic pharmaceutical formulations.

The term "natural wax" refers to one or more long chain fatty ester compounds found in natural environments such as plants, seeds and grains, or derived from animals or insects, e.g., sheep or honey bees. The term "natural wax" also refers to alkoxylated derivatives of one or more long chain fatty ester compounds found in natural environments such as plants, seeds and grains, or derived from animals or insects.

The invention is directed to a poly(nitrogen/amine) derivative of a natural wax of formula I

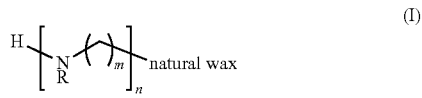
(I)

wherein R is —H, —CH$_3$, —C$_2$H$_5$, —OH and —CH$_2$OH; m is 2, 3, 4, 5 or 6; n is an integer from 8 to 110 if m is 2 or 3, and n is an integer from 6 to 60 if m is 4, 5 or 6.

Some of the more preferred natural waxes include beeswax, lanolin, PEG lanolin, jojoba and PEG jojoba. The poly(nitrogen/amine) derivative will likely have a number average molecular weight of from 600 daltons to 10,000 daltons, or from 1200 daltons to 6000 daltons.

The invention is directed to ophthalmic compositions including contact lens care solutions comprising an effective amount of poly(nitrogen/amine) derivative of a natural wax of formula (I). In one embodiment, the natural wax is selected from the group consisting of beeswax, lanolin, PEG lanolin, jojoba and PEG jojoba. The poly(nitrogen/amine) derivative can have a number average molecular weight of from 600 daltons to 10,000 daltons or from 1200 daltons to 6000 daltons.

The poly(nitrogen/amine) derivatives of formula I can be prepared by reacting polyethylene glycol lanolin (PEG lanolin) or polyethylene glycol jojoba (PEG jojoba) with a polycationic nitrogen/amine oligomer. The PEG lanolin and PEG jojoba are commercially available. See, Examples 1 and 2. Likewise, the poly(nitrogen/amine) derivatives of formula I can be prepared by reacting commercially available lanolin or commercially available jojoba with a polycationic nitrogen/amine oligomer. See, Examples 3 and 4.

In the case of a contact lens care solution, the concentration by weight of the poly(nitrogen/amine) derivative of a natural wax of formula I in the solution should be 10 to 1,000 times the concentration by weight of the cationic antimicrobial component. In addition, the number average molecular weight of the poly(nitrogen/amine) derivative of a natural wax of formula I should be similar to the number average molecular weight of the antimicrobial component. Accordingly, a ratio of the average number molecular weight of the poly(nitrogen/amine) natural wax ($M_{NW}$) to the average number molecular weight of the antimicrobial component ($M_{NA}$) is from 5:1 to 1:5, or from 3:1 to 1:3.

The poly(nitrogen/amine) derivative of lanolin or jojoba is present in a contact lens care solution from 0.0001 wt. % to 2 wt %, from 0.001 wt. % to 0.5 wt. % or from 0.01 wt. % to 0.1 wt. %. As expected, the amount of the derivatized natural wax of formula I added to the solution will depend on a number of different factors such as the type of cationic antimicrobial component(s) present in the solution and their respective concentrations. In most cases, the concentration by weight of the derivatized natural wax in the solution will be at least ten (10) times greater than the concentration by weight of the cationic antimicrobial component(s). Typically, the described lens care solutions will have a concentration by weight of the derivatized natural wax that is 10 to 400 times the concentration by weight of the cationic antimicrobial component(s).

In many embodiments, the derivatized nitrogen/amine of lanolin is present in the ophthalmic compositions at a preferred concentrations of from 0.005 wt. % to 0.8 wt. %, from 0.005 wt. % to 0.4 wt. %, and from 0.005 wt. % to 0.1 wt. %.

In many embodiments, the derivatized nitrogen/amine jojoba is present in the ophthalmic compositions at a preferred concentrations of from 0.005 wt. % to 2.0 wt. %, from 0.005 wt. % to 1.0 wt. %, and from 0.06 wt. % to 0.4 wt. %.

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

In ophthalmic compositions, typically, formulated to be dispensed directly to the eye via drops, the hyaluronic acid is present in the compositions from 0.02 wt. % to 0.2 wt. %. In contact lens cleaning and disinfecting solutions, typically, formulated to be dispensed into a contact lens case, the hyaluronic acid is present in the compositions from 0.002 wt. % to 0.02 wt. %.

Guar gum is the ground endosperm of *Cyamopisis tetragonolobus* (L.) Taub. The water soluble fraction (85%) is called "guaran" (molecular weight of 220,000), which consists of linear chains of (1-4)-β-D mannopyranosyl units with α-D-galactopyranosyl units attached by (1-6) linkages. The ratio of D-galactose to D-mannose in guaran is about 1:2. The gum is primarily used in food and personal care products for its thickening property, and it has five to eight times the thickening power of starch. Guar gum may be obtained, for example, from Rhone-Polulenc (Cranbury, N.J.). Guar gum can also be derivatized to modify its properties, for example, guar derivatives such as those containing hydroxypropyl or hydroxypropyltrimonium chloride substitutions have been commercially available for over a decade. Derivatized guar of various degree of substitution are also commercially available from Rhone-Poulenc. Hydroxypropyl guar, preferably with low molar substitution (e.g., less than 0.6), is of particular interest in the ophthalmic compositions described herein.

In ophthalmic compositions, typically, formulated to be dispensed directly to the eye via drops, the hydroxypropyl guar is present in the compositions from 0.05 wt. % to 0.5 wt. %. In contact lens cleaning and disinfecting solutions, typically, formulated to be dispensed into a contact lens case, the hydroxypropyl guar is present in the compositions from 0.005 wt. % to 0.06 wt. %.

As stated, dry eye syndrome is typically defined as an ocular condition in which patients can sense a burning, a feeling of dryness, or a persistent irritation or tearing of the eyes. Many suspect that dry eye arises from tear deficiency or excessive tear evaporation that causes damage to the interpalpebral ocular surface. The tear film has a thin layer of lipid (about 70 nm thick in healthy eyes) that covers the aqueous layer. The lipid layer is believed to thicken the aqueous subphase, to retard evaporation, to provide a smooth optical surface for the cornea, to provide a barrier against foreign particles including microbes, and to seal the lid margins during prolonged closure. Eye drops that are formulated to stabilize the lipid layer may help relieve symptoms of dry eye.

The combination of the derivatized nitrogen/amine natural waxes, particularly with hyaluronic acid, or hydroxypropyl guar, can be used to stabilize the thin layer of lipid of the tear film, and consequently, minimize evaporative loss of moisture from the ocular surface. In this regard, one embodiment of the invention is directed to ophthalmic compositions that comprise 0.005 wt. % to 2.0 wt. % of a derivatized nitrogen/amine natural wax of formula I in combination with 0.002 w. % to 0.2 wt. % hyaluronic acid or 0.05 w. % to 0.5 wt. % hydroxypropyl guar. In many instances, if the derivatized nitrogen/amine natural wax is derived from lanolin, the derivatized lanolin is present in the ophthalmic compositions at a preferred concentrations of from 0.005 wt. % to 0.8 wt. %, from 0.005 wt. % to 0.4 wt. %, and from 0.005 wt. % to 0.1 wt. %. In many instances, if the derivatized nitrogen/amine natural wax is derived from jojoba, the derivatized jojoba is present in the ophthalmic compositions at a preferred concentrations of from 0.005 wt. % to 2.0 wt. %, from 0.005 wt. % to 1.0 wt. %, and from 0.06 wt. % to 0.4 wt. %.

Soft disposable contact lenses are commonly sold in disposable packages. The traditional blister pack packaging for disposable lenses (monthly, bi-weekly and daily) consists of a plastic receptacle for the lens (herein after referred to as a "boat"), topped by a sealing film. The boat is filled with a suitable storage solution, preferably saline, and includes a single lens in situ. The blister pack is then autoclaved using steam and pressure to achieve sterility. In some instances, a storage solution will include one or more polymers selected from the group consisting of polyvinyl alcohols and their derivatives, polysaccharides and their derivatives, and also cellulose derivatives. In addition to one or more polymers identified above, the solution can also include other components known to be present in natural tears, such as calcium, potassium and/or magnesium ions.

The derivatized nitrogen/amine natural waxes described herein are also very effective components of a contact lens packaging solution. This is particularly the case for balafilcon A contact lenses sold by Bausch+Lomb as PureVision® extended wear lenses. Balafilcon A is classified as an ionic, silicon hydrogel contact lens material, and the material is known to interact strongly with cationic oligomers or polymers. The derivatized nitrogen/amine natural waxes of formula I are chemically designed to form strong surface interactions with balafilcon A lenses. The polycationic tail of the derivatized natural waxes interacts strongly with the anionic surface regions of the lenses, and essentially anchors the natural wax to the surface of the lens. Accordingly, the derivatized nitrogen/amine natural waxes are localized on the surface of the lenses. First, the anchored natural waxes minimize the deposition of denatured lipids on the surface of the lenses over an extended wear time. Second, the anchored natural waxes minimize the amount of cationic antimicrobial components of a contact lens care solution that is absorbed into the lens. Third, the anchored natural wax is believed to stabilize the tear film, and thereby provide a patient with an extended window of comfortable contact lens wear.

A package solution that includes a derivatized nitrogen/amine natural waxes described herein is often based on a buffered saline solution well known in the art of contact lens manufacturing. The package solution is added to a contact lens package near the end of a manufacturing line after the contact lens has been processed to remove chemical impurities. The solution packaged lens is then sealed and sterilized in the presence of the derivatized nitrogen/amine natural wax.

Applicants and others at Bausch & Lomb have developed and tested numerous ophthalmic compositions for use as contact lens care solutions. Lens care solutions must satisfy a number of functional characteristics. First, the solutions must possess the cleaning ability to remove denatured tear proteins and tear lipids as well as other external contaminants. Second, the solutions must possess significant disinfecting ability against a number of different bacteria and fungal strains. Third, the solutions must remain comfortable to the contact lens patient with minimal stinging as well as provide a platform to provide additional comfort or protection to the ocular surface. Lastly, the solutions must not cause significant shrinkage or swelling of the many different contact lens materials, which in turn can lead to loss in visual acuity and unwanted or pronounced lens movement. In addition, the stabilization or maintenance of tear film is not only important for the treatment of dry eye syndrome, but also important to improve sensations of comfort and hydration in those patients that wear contact lenses. Most of the lens care solutions described herein satisfy each of the functional characteristics described above.

A contact lens cleaning and disinfecting solution will also include one or more antimicrobial components selected from poly(hexamethylene biguanide) (PHMB or PAPB), α-[4-tris (2-hydroxyethyl)-ammonium chloride-2-butenyl]poly[1-dimethyl ammonium chloride-2-butenyl]-ω-tris(2-hydroxyethyl) ammonium chloride (polyquaternium-1), and 1,1'-hexamethylene-bis[5-(2-ethylhexyl)biguanide], which is referred to in the art as "alexidine". A commercial source of a PHMB can be obtained from Arch Chemicals, Inc., Norwalk, Conn. under the trademark Cosmocil™ CQ. The PHMB is present in the compositions from 0.2 ppm to 2 ppm or from 0.5 ppm to 1.5 ppm. The polyquaternium-1 is present from 1 ppm to 10 ppm or from 1 ppm to 3 ppm. The alexidine is present in the compositions from 0.5 ppm to 5 ppm or from 0.5 ppm to 2 ppm.

It is to be understood by those in the art that the compositions can include one or more of the antimicrobial components described above. For example, in one embodiment, a contact lens care solution can include polyquaternium-1 in combination with a biguanide antimicrobial component such as poly(hexamethylene biguanide) or alexidine. The polyquaternium-1 is present in relatively low concentrations, that is, from 0.5 ppm to 3 ppm, relative to the reported concentration of polyquaternium-1 in both Opti-Free®Express and Opti-Free®Replenish. Applicants believe that the polyquaternium-1 and the biguanide, in combination, can enhance the biocidal profile of the solutions.

Polyquaternium-42 is another known antimicrobial component, and is present in the ophthalmic compositions from 5 ppm to 50 ppm. Polyquaternium-42 is often used in combination with PHMB, polyquaternium-1, or alexidine, or in combination with a stabilized from of chlorine oxide such as a metal chlorite.

The contact lens care solutions or ophthalmic compositions will likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, a viscosity inducing or thickening component, a chelating or sequestering component, or a tonicity component. The additional component or components can be selected from materials which are known to be useful in contact lens care solutions and are included in amounts effective to provide the desired functional characteristic.

Suitable surfactants can be cationic or nonionic, and are typically present (individually or in combination) in amounts up to 1.4% w/v. One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred surfactant is tyloxapol.

A particular non-ionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The foregoing poly(oxyethylene) poly(oxypropylene) block polymer surfactants will generally be present in a total amount from 0.0 to 2% w/v, from 0. to 1% w/v, or from 0.2 to 0.8% w/v An analogous of series of surfactants, for use in the lens care compositions, is the poloxamer series which is a poly(oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

Another poloxamer-type series of surfactants of interest are referred to as an ethyleneoxide-butyleneoxide (EO-BO) block copolymer of the formula $(EO)_m(BO)_n$ where m is an integer having an average value of 10 to 1000 and n is an integer having an average value of 5 to 1000. It is believed that the ethyleneoxide butyleneoxide block copolymers interact with hyaluronic acid in the aqueous lens care compositions. Aqueous compositions comprising EO-BO copolymers are generally Newtonian in behavior, and EO-BO copolymer contributes little to the viscosity of such composition at the relatively low concentrations present in such concentrations. However, the hyaluronic acid and EO-BO copolymers have a synergistic increase in viscosity relative to compositions comprising hyaluronic acid or EO-BO alone. Compositions with hyaluronic acid and EO-BO compositions have desirable viscoelastic and interfacial properties that make them well suited for contact lens care applications such as for disinfection and rewetting of contact lenses.

EO-BO block copolymers are somewhat more hydrophobic in aqueous solutions than the corresponding ethyleneoxide-propyleneoxide copolymers sold under the trademark Pluronics® and Tetronics®. The preferred copolymers of formula $(EO)_m(BO)_n$ are those wherein there is a predominance of EO to BO segments. That is, the variable "m" in the above formula is preferably greater than the variable "n". The EO-BO block copolymers will preferably have a ratio of EO to BO segments of from about 2:1 to about 10:1, with a ratio of about 3:1 to about 6:1 being most preferred. At an air-water interface these nonionic surfactants form elastic layers that can provide a cushioning effect for contact lenses when used in ophthalmic solutions. In a preferred embodiment, the compositions described herein include an EO-BO block copolymer and hyaluronic acid. Some ophthalmic applications of such compositions include contact lens disinfection solutions, dry eye and artificial tear compositions. The EO-BO copolymer can be present at a concentration of 0.001 wt. % to 0.6% wt. %, or from 0.05 wt. % to 0.2% wt. %.

In another embodiment, the surfactant is a an amphoteric surfactant of general formula A

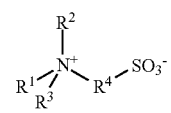

A wherein $R^1$ is R or —$(CH_2)_n$—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$alkylene optionally substituted with hydroxyl. Alternatively, one can use a hydroxysulfobetaine of general formula B

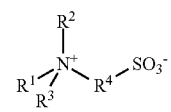

B wherein $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v. As taught by U.S. Pat. No. 6,172,017, the presence of the sugar alcohols can assist in the removal of protein deposits from the surface of soft contact lenses.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator Na$_2$EDTA or a possible combination with Na$_2$EDTA, is a disuccinate of formula IV below or a corresponding salt thereof;

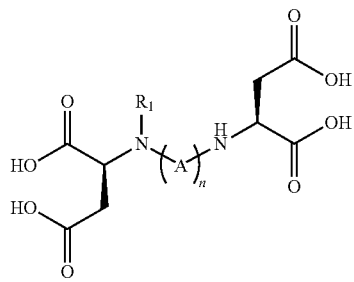

IV wherein R$_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

One exemplary contact lens care solution prepared with the components and amounts of each listed in Table 1.

TABLE 1

| Component | Minimum Amt. (wt. %) | Maximum Amt. (wt. %) | Preferred Amt. (wt. %) |
|---|---|---|---|
| boric acid | 0.10 | 1.0 | 0.64 |
| sodium borate | 0.01 | 0.20 | 0.09 |
| sodium chloride | 0.05 | 1.0 | 0.4 |
| PEI jojoba or PEI lanolin | 0.005 | 1.0 | 0.1 |
| poloxamine or poloxamer | 0.05 | 1.0 | 0.6 |
| PHMB | 0.5 ppm | 2 ppm | 1.1 ppm |
| polyquaternium-1 | 0.5 ppm | 5 ppm | 1 ppm |

Another contact lens care solution includes the following ingredients listed in Table 2.

TABLE 2

| Component | Minimum Amt. (wt. %) | Maximum Amt. (wt. %) | Preferred Amt. (wt. %) |
|---|---|---|---|
| dexpanthenol | 0.3 | 3.0 | 1.5 |
| poloxamine or poloxamer | 0.05 | 1.0 | 0.1 |
| TRIS | 0.10 | 0.8 | 0.46 |
| PEI jojoba or PEI lanolin | 0.005 | 1.0 | 0.1 |
| PHMB | 0.5 ppm | 2 ppm | 1 ppm |
| Polyquaternium-1 | 1 ppm | 3 ppm | 1 ppm |

Another contact lens care solution includes the following ingredients listed in Table 3.

TABLE 3

| Component | Minimum Amt. (wt. %) | Maximum Amt. (wt. %) | Preferred Amt. (wt. %) |
|---|---|---|---|
| Tetronics ® 1304 | 0.01 | 0.2 | 0.05 |
| boric acid | 0.1 | 1.0 | 0.6 |
| sodium citrate | 0.01 | 0.4 | 0.15 |
| PEI jojoba or PEI lanolin | 0.02 | 0.6 | 0.08 |
| polyquaternium-1 | 2 ppm | 10 ppm | 5 ppm |

Still another contact lens care solution includes the following ingredients listed in Table 4.

TABLE 4

| Component | Minimum Amt. (wt. %) | Maximum Amt. (wt. %) | Preferred Amt. (wt. %) |
|---|---|---|---|
| poloxamine or poloxamer | 0.05 | 1.0 | 0.10 |
| boric acid | 0.10 | 1.0 | 0.6 |
| PEI jojoba or PEI lanolin | 0.005 | 1.0 | 0.1 |
| alexidine | 1 ppm | 4 ppm | 3 ppm |
| Polyquaternium-1 | 1 ppm | 4 ppm | 2 ppm |

As described, the ophthalmic compositions can be used to clean and disinfect contact lenses as a daily care regimen. The procedure includes removing the contact lens from the eye, adding a few drops of the solution to each side of the lens, followed by gently rubbing the surface between ones fingers for approximately 3 to 10 seconds, rinsing both sides of the lens with a few milliliters of solution and placing the lens in a lens storage case. The lens is then immersed in fresh solution for at least two hours. The lens is then removed from the case, optionally rinsed with more solution, and repositioned on the eye.

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

The ophthalmic compositions can also be formulated as a contact lens rewetting eye drop solution. By way of example, the rewetting drops may be formulated according to any one of the foregoing formulations of Tables 1 to 3 above. Alternatively, the formulations may be modified by increasing the amount of surfactant; by reducing the amount of antimicrobial agent to a preservative amount and/or by adding a humectant and/or demulcent.

The ophthalmic compositions can be used as a preservative in formulations for treating patients with dry eye or other ocular disorders. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents. Often it will be advantageous to use lauramine oxide as a secondary preservative agent in ophthalmic compositions The Preparation of the Poly(Ethyleneimine) Derivatives of a Natural Wax.

An aqueous solution of branched poly(ethyleneimine) (PEI, BASF-SE) with a molecular weight of $M_w$=1,300 is prepared. Generally, the branched PEI includes primary, secondary and tertiary, groups in the ratio of 1:2:1 and that their branching sites are separated mainly by secondary amine groups (one branch for every 3-3.5 N atom within a linear chain).

Alternatively, linear poly(ethyleneimine) can be used as a source of nitrogen/amine oligomer. The linear poly(ethyleneimine) prepared using the procedure described by R. Hoogenboom, *Macromolecules* 2010, 43, 927-33. The Hoogenboom article describes the synthesis of poly(ethyleneimine) with an average number molecular weight of about 2500 daltons to about 14,000 daltons.

An aqueous solution of a poly(ether) is prepared. In one instance, the poly(ether) is a relatively low molecular weight poloxamer also available from BASF. The poloxamer that is used will typically have an average molecular weight from 1000 to 5000. In another instance the poly(ether) is a polyethylene glycol with a relatively low molecular weight from 1000 to 6000. In still another instance, the poly(ether) is a polyethylene oxide derivative of a natural wax selected from lanolin or jojoba—often referred to in the art as PEG-lanolin and PEG-jojoba, respectively. PEG75-lanolin can be obtained from Kao Chemicals. PEG150-jojoba can be obtained from Floratech® Americas.

Example 1

Synthesis of poly(ethyleneimine)-PEG-lanolin

The free hydroxyl group of the polyether chain of PEG75-lanolin is first activated by reaction with 1,1'-carbonyldiimidazole. The activated PEG75-lanolin is than linked to the free amino group of the poly(ethyleneimine) to form the desired PEI-PEG-lanolin.

Example 2

Synthesis of poly(ethyleneimine)-PEG-jojoba

The free hydroxyl group of the polyether chain of PEG150-jojoba is first activated by reaction with 1,1'-carbonyldiimidazole. The activated PEG150-jojoba is than linked to the free amino group of the poly(ethyleneimine) to form the desired PEI-PEG-jojoba.

Example 3

Synthesis of PEI-lanolin

The free acid groups of the natural wax lanolin is first activated by reaction with 1,1'-carbonyldiimidazole. The activated lanolin is than linked to the free amino group of the poly(ethyleneimine) to form the desired PEI-lanolin.

Example 4

Synthesis of PEI-jojoba

The free acid groups of the natural wax jojoba is first activated by reaction with 1,1'-carbonyldiimidazole. The activated jojoba is than linked to the free amino group of the poly(ethyleneimine) to form the desired PEI jojoba.

Example Nos. 5 to 9

Contact lens care solutions of Example Nos. 5 to 10 of Table 4 are prepared using the following process (components are listed in wt. % unless noted in ppm). A volume of purified water equivalent to 70-90% of the total batch weight is added to a stainless steel mixing vessel. The following batch quantities of components are added to the water with stirring in the order listed: sodium chloride, edetate disodium, boric acid, sodium borate, the poly(ethyleneimine) lanolin. The solution is mixed (stirred) for not less than 10 minutes to ensure complete dissolution of each of the components. If sodium hyaluronate is to be added, the solution is warmed to a temperature not less than 70° C. and then the sodium hyaluronate is added. The warmed solution is stirred for at least 20 minutes until the sodium hyaluronate appears to be completely dissolved. The pH of the resulting solution is measured at room temperature, and if necessary, the pH is adjusted with 1N NaOH or 1N HCl (target pH=7.5). In a second stainless steel vessel, a measured amount a measured amount of PHMB required for the batch is added to a given amount of purified water, and the solution is stirred for at least 10 minutes.

TABLE 4

| Example | 5 | 6 | 7 | 8 | 9 |
|---|---|---|---|---|---|
| boric acid | 0.60 | 0.55 | 0.64 | 0.65 | 0.64 |
| sodium borate | 0.105 | 0.11 | 0.12 | 0.09 | 0.09 |
| sodium chloride | 0.50 | 0.45 | 0.50 | 0.40 | 0.5 |
| Na$_2$EDTA | 0.08 | 0.08 | 0.06 | 0.05 | 0.05 |
| sodium hyaluronate | — | — | 0.01 | 0.01 | — |
| Ex. 3, PEI-lanolin | 0.03 | 0.02 | 0.03 | 0.02 | 0.03 |
| PHMB (ppm) | 1.3 | 1.3 | — | — | — |
| polyquaternium-1 | — | 1.0 | 2.0 | 2.0 | 10 |
| lauramine oxide | — | — | 80 | — | — |
| alexidine | — | — | — | 3.0 | — |

Example Nos. 10 to 14

Example Nos. 10 to 14 are prepared in accordance with the procedure and component concentrations used for Examples 5 to 9 with the exception that Example 4, PEI-jojoba was substituted for the PEI-lanolin.

Example Nos. 15 to 19

Example Nos. 15 to 19 are prepared in accordance with the procedure and component concentrations used for Examples 5 to 9 with the exception that PEI-PEG75-lanolin of Example 1 was substituted for the PEI-lanolin.

Example Nos. 20 to 24

Example Nos. 20 to 24 are prepared in accordance with the procedure and component concentrations used for Examples 5 to 9 with the exception that PEI-PEG150-jojoba of Example 2 was substituted for the PEI-lanolin.

The invention claimed is:

1. An ophthalmic composition aqueous-based solution comprising 0.005 wt. % to 2.0 wt. % of a poly(nitrogen/amine) derivative of a natural wax of formula (I)

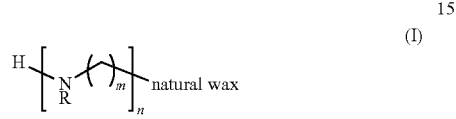

(I)

wherein R is —H, —CH3, —C2H5, —OH and —CH2OH; m is 2, 3, 4, 5 or 6; n is an integer from 8 to 110 if m is 2 or 3, and n is an integer from 6 to 60 if m is 4, 5 or 6.

2. The composition of claim 1 wherein the natural wax is selected from the group consisting of beeswax, lanolin, PEG lanolin, jojoba and PEG jojoba.

3. The composition of claim 1 further comprising 0.002 w. % to 0.2 wt. % hyaluronic acid or 0.05 w. % to 0.3 wt. % hydroxypropyl guar.

4. The composition of claim 2 further comprising 0.002 w. % to 0.2 wt. % hyaluronic acid or 0.05 w. % to 0.3 wt. % hydroxypropyl guar.

5. The composition of claim 1 wherein the poly(nitrogen/amine) derivative of a natural wax is polyethyleneimine lanolin, the polyethyleneimine lanolin present from 0.005 wt. % to 0.3 wt. %.

6. The composition of claim 5 wherein the polyethyleneimine lanolin has a weight average molecular weight from 600 daltons to 6000 daltons.

7. The composition of claim 1 wherein the poly(nitrogen/amine) derivative of a natural wax is polyethyleneimine jojoba, the polyethyleneimine jojoba is present from 0.005 wt. % to 1.0 wt. %.

8. The composition of claim 7 wherein the polyethyleneimine jojoba has a weight average molecular weight from 600 daltons to 6000 daltons.

9. The composition of claim 1 wherein the composition further comprises a pharmaceutical agent.

10. The composition of claim 1 further comprising dexpanthenol, sorbitol, xylitol, glycolic acid, propylene glycol, 2-amino-2-methyl-1,3-propanediol, poly(ethyleneoxide-butyleneoxide) or any mixture thereof.

11. The composition of claim 1 further comprising one or more antimicrobial components selected from the group consisting poly(hexamethylene biguanide), which is present from 0.5 ppm to 1.5 ppm; α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm; and alexidine, which is present from 1 ppm to 4 ppm.

12. The composition of claim 4 further comprising one or more antimicrobial components selected from the group consisting poly(hexamethylene biguanide), which is present from 0.5 ppm to 1.5 ppm; α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm; and alexidine, which is present from 1 ppm to 4 ppm.

13. The composition of claim 1 further comprising 0.5 ppm to 1.5 ppm of poly(hexamethylene biguanide), or 1 ppm to 4 ppm alexidine,
wherein the poly(nitrogen/amine) derivative of a natural wax of formula (I) reduces an amount of the poly(hexamethylene biguanide), or alexidine, that is absorbed into a balafilcon A silicone hydrogel contact lens by at least 25% relative to an equivalent composition but in the absence of the derivatized natural wax, following a soak of the balafilcon A lens in the composition and the equivalent composition for six hours.

14. The composition of claim 13 further comprising α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 3 ppm.

15. A method of treating a patient with dry eyes, the method comprising instructing a patient to administer one or more eye drops of an ophthalmic composition aqueous-based solution comprising 0.005 wt. % to 2.0 wt. % of a poly(nitrogen/amine) derivative of a natural wax of formula I

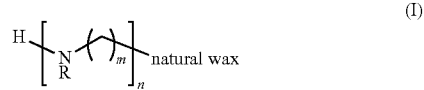

(I)

wherein R is —H, —CH3, —C2H5, —OH and —CH2OH; m is 2, 3, 4, 5 or 6; n is an integer from 8 to 110 if m is 2 or 3, and n is an integer from 6 to 60 if m is 4, 5 or 6.

16. The method of claim 15 wherein the natural wax is selected from the group consisting of beeswax, lanolin, PEG lanolin, jojoba and PEG jojoba.

17. The method of claim 15 wherein the patient wears contact lenses and the one or more drops are administered directly to the lenses positioned in the eye of the patient.

18. The composition of claim 1, wherein the poly(nitrogen/amine) derivative of a natural wax of formula (I) is a branched poly(ethyleneimine) or linear poly(ethyleneimine) derivative of a natural wax.

19. The composition of claim 1, wherein the poly(nitrogen/amine) derivative of a natural wax of formula (I) is a branched poly(ethyleneimine) derivative of a natural wax.

20. The composition of claim 1, wherein the poly(nitrogen/amine) derivative of a natural wax of formula (I) is a linear poly(ethyleneimine) derivative of a natural wax.

* * * * *